United States Patent [19]

Stich-Baumeister et al.

[11] Patent Number: 4,872,759
[45] Date of Patent: Oct. 10, 1989

[54] SENSOR FOR GASES OR IONS

[75] Inventors: Eva-M. Stich-Baumeister, Erlangen; Karl-Otto Dohnke, Forchheim-Kersbach; Albrecht Winnacker, Erlangen, all of Fed. Rep. of Germany

[73] Assignee: Siemens Aktiengesellschaft, Munich, Fed. Rep. of Germany

[21] Appl. No.: 216,134

[22] Filed: Jul. 7, 1988

[30] Foreign Application Priority Data

Jul. 8, 1987 [DE] Fed. Rep. of Germany ....... 3722449

[51] Int. Cl.$^4$ ........................................... G01N 21/00
[52] U.S. Cl. ................................................... 356/432
[58] Field of Search ........................... 356/5, 28.5, 432

[56] References Cited

U.S. PATENT DOCUMENTS

| 3,754,867 | 8/1973 | Guenther. | |
|---|---|---|---|
| 4,448,524 | 5/1984 | Brus et al. | 356/432 |
| 4,600,310 | 7/1986 | Cramp et al. | 356/432 |
| 4,661,320 | 4/1987 | Ito et al. | 356/432 |

Primary Examiner—Léon Scott, Jr.
Attorney, Agent, or Firm—Kenyon & Kenyon

[57] ABSTRACT

A sensor for gases or ions with a light source, a detector and a sensor layer all of which are attached to a carrier. A thin sensor film, the absorptivity of which changes through the action of the measurement medium, is arranged on a light waveguide, the one flat side of which covers a flat end face of the light source, the end face of the carrier and a plane receiving surface of the detector. Thus, a sensitive sensor, especially for gases, is obtained in which the sensor layer, the light source and the detector form an integrated structural unit.

28 Claims, 1 Drawing Sheet

SENSOR FOR GASES OR IONS

BACKGROUND OF THE INVENTION

This invention relates to a sensor for gases and/or ions which uses a light source, a detector, and a sensor layer all mounted upon a single carrier body.

It is known that certain substances are suitable for measuring the partial pressure of gases and vapors and that these substances can be arranged in a test tube. However, continuous determination of the relevant gas component is not possible with these test tubes. Although mass spectrometers permit continuous measurements, the accuracy obtainable with these expensive devices is frequently not necessary.

One known embodiment of a thin-film sensor for determining the carbon dioxide content in air contains a thin sensor layer which is arranged on a carrier. The flat side of the carrier facing the sensor layer is provided with a mirror surface. The light ray of a radiation source physically separated from the sensor layer and the carrier passes through the sensor layer, is reflected at the mirror surface of the carrier and then arrives at a photoelectric converter which is likewise physically separated from the sensor and the carrier and which may be a photo cell. The light ray therefore passes through the gas sensitive sensor layer twice, the absorptivity of which is changed by the action of the gas. The corresponding color deviation of the light ray is registered by the photo cell. See Guenther U.S. Pat. No. 3,754,867, issued August, 1973.

In a known embodiment of a gas sensor for hydrogen and hydrogen compounds, a light source such as a light-emitting diode LED is connected via a light waveguide, designed as a thin film, to a detector such as a photo diode. The light waveguide is arranged on a substrate and provided with a superficial layer of a catalytic metal such as palladium (Pd) or platinum (Pt), which is subjected to the action of the gas. The light waveguide serves as a sensor and consists of a metal oxide, for example, tungsten oxide ($WO_3$) or molybdenum oxide ($MoO_3$). The hydrogen protons penetrate the metal layer where they are absorbed and dissociated. The hydrogen atoms released chemically reduce the sensor layer, which thereby changes its absorptivity. To enhance the absorption, the sensor is heated. See Ito, et al. U.S. Pat. No. 4,661,320, issued Apr. 28, 1987.

SUMMARY OF THE INVENTION

It is an object of the invention to simplify the known embodiments of these sensors. In particular, it is desirable that the sensor operate at room temperature.

According to the invention, the light source and the photo detector are connected to each other via the light waveguide which serves to conduct the radiation and is in turn covered with the sensor layer. The light source and the detector can be fastened, in particular cemented, to the light-impervious and mechanically strong carrier in such a manner that their respective end faces are at least approximately in a single plane. The light entering the light waveguide and how it is changed by the action of ions at the surface of the sensor layer or the action of gases in the volume of the sensor layer is registered by the detector.

This sensor arrangement is thus based on a different measuring principle than the ones used in previous sensors. The attenuated total reflection of the sensor layer as applied to the light waveguide is measured, not the absorptivity of the sensor layer.

In a particular embodiment of the sensor, a matching layer can be provided between the light source and the light waveguide which matching layer can consist of an altraviolet-hardening adhesive. A matching layer can also be arranged between the light waveguide and the detector; it can likewise consist of an ultraviolet-harding adhesive.

In order to limit light losses, the flat side of the light waveguide facing away from the light source can be provided with a mirror surface in the proximity of the end face of the light source.

In the embodiment where the sensor is used as a gas sensor, an optical filter with reversible color change, preferably consisting of a mixture of at least one alkaline or acid color former or pigment and at least one complementary acid or alkaline compound (See De-OS 35 06 676), is used. Particularly advantageous is a color former or a pigment of the triphenylmethane system, particularly crystal violet lacton. A suitable pigment is phthalein or sulfonephthalein. As the acid compound, the sensor layer can contain bisphenol-A or salicic acid. As an alkaline compound, p-toluolidene or p-chloroanilin is suitable. The mixture can also be embedded in a matrix substance which may consist of polyvinyl-chloride (PVC) polyethylene or silicone.

In the embodiment where the sensor is used as an ion sensitive sensor, for example, a sensor for a pH value, the sensor layer can also consist of an indicator pigment.

With a III-V semiconductor it is possible to design the entire sensor as a light waveguide and an integrated optoelectronic component. This means a substantial simplification and, in particular, also a substantial improvement with respect to the response time.

BRIEF DESCRIPTION OF THE DRAWINGS

For a further explanation of the invention, reference is made to the drawings, in which embodiments of a sensor according to the invention are schematically illustrated.

DETAILED DESCRIPTION

Figure 1:
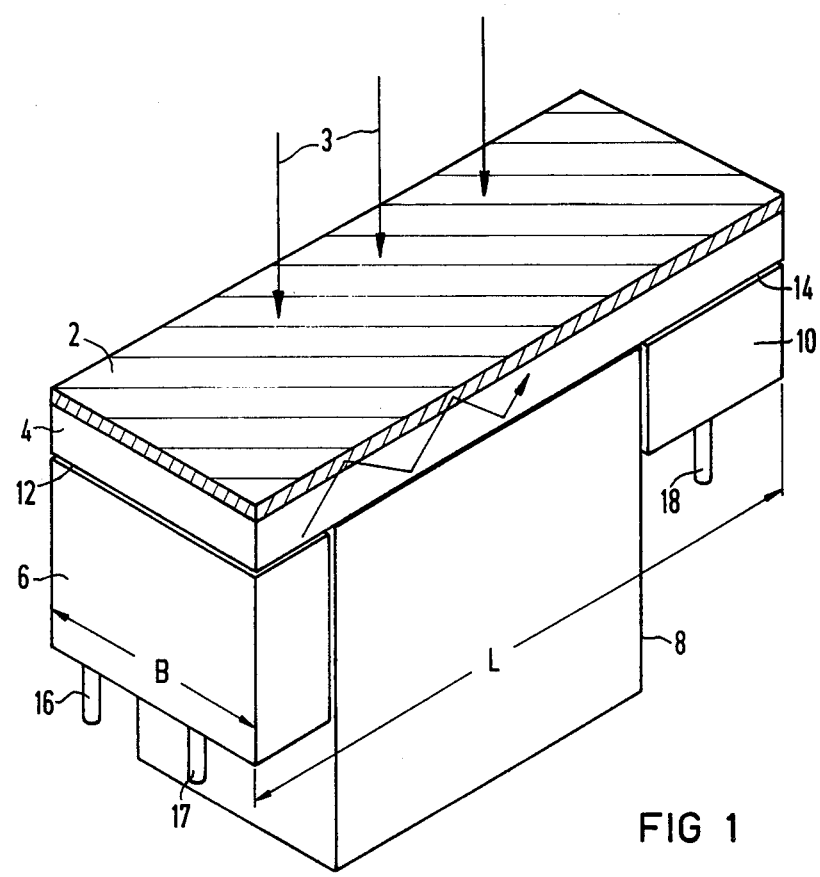
FIG. 1 shows a sensor in perspective view.

In the embodiment of the sensor for gases or ions shown in FIG. 1, a thin sensor layer 2, the absorptivity of which layer changes with contact with the gas being measured (the gas is indicated by arrows 3), is arranged on a light waveguide 4, the layer and waveguide having length L of approximately 20 mm and a width B of approximately 5 mm. On the lower flat side of the waveguide 4, a light source 6 is arranged in such a manner that one end of the light waveguide 4 covers the light generating face of the light source 6. Similarly, the lower flat side of the other end of the waveguide 4 covers the end face of a detector 10. The light source 6 and the detector 10 are fastened on to respective narrow sides of carrier 8 by, for example, cementing them to the end faces of the carrier to which the light waveguide 4 is also fastened.

Sensor layer 2 is preferably at least 50 nm and not more than 200 nm thick and can consist of a conventional ion-sensitive material for components of a liquid medium or of a chemosensitive material for gases and vapors. Preferably the sensor comprises an optochemical gas sensor for gases and vapors. Well suited for the detection of gases and vapors is an optical filter with a reversible color or transparency change, the sensor containing a mixture of at least one alkaline or acid color former and at least one complementary acid or alkaline compound such as is disclosed in German Patent Application No. 35 06 686. The light waveguide 4 serves for conducting the light between the light source 6 and the detector 10, and consists of a material which is opaque at the light wavelength of light source 6 and which adheres well to the sensor layer 2. It preferably consists of a III-V compound semiconductor material, particularly gallium phosphide (GaP), gallium arsenide (GaAs) or gallium arsenide phosphide $(GaAs_{(1-x)}P_x)$. The two flat sides of the light waveguide 4 are planar and have only a very small roughness depth. A light-emitting diode with a large planar light exit area and approximately the same width as the light waveguide 4 is preferred as light source 6. The wavelength of the diode should be in the absorption range of sensor layer 2. If a yellow light-emitting diode is used, sensor layer 2 will be an optical filter containing, for example, crystal violet lacton and bisphenol-A in a ratio of about 1:7.5. If a red light-emitting diode is used as light source 6, sensor layer 2 will be an optical filter containing malachite-green lacton and bisphenol-A in a ratio 1:5. In both embodiments, sensor layer 2 can contain up to about 25% by weight polyvinylchloride (PVC). The material of the optical filter is generally processed as a solution which can be centrifuged onto the light waveguide 4 by a varnish centrifuge into a homogenous layer of uniform thickness. Detector 10 can be a photo diode or a photo transistor, the receiving area of which comprises approximately the entire width of the light waveguide 4. Carrier 8 is comprised of an opaque mechanically strong material which is preferably electrically conductive and can be used simultaneously as the common ground for light source 6 and detector 10. When carrier 8 is made of plastic, for example, polymethylmethacrylate (Plexiglass), the end face of carrier 8 can be provided with an opaque overlay.

In a special embodiment of the sensor, a layer for matching the index of refraction (index matching) can be provided between the end face of the light source 6 and the light waveguide 4, which would preferably simultaneously also serve as an adhesive layer and can consist, for example, of an ultraviolet-hardening adhesive. This matching layer 12 is particularly advantageous for coupling the light emitted from light source 6 into the light waveguide 4. Similarly, a matching layer 14 can be provided between light waveguide 4 and the end face of detector 10, the index of refraction of layer 14 being between the index of refraction of waveguide 4 and the casting compound of the detector 10 and may be an ultraviolet-hardening adhesive. The connecting power leads to light source 6 are indicated as 16 and 17.

When sensor layer 3 is an optical filter, the color of sensor layer 2 fades through reaction with the gas, and the absorption of the sensor layer 2 decreases. The corresponding intensity increase of the light transmitted by light waveguide 4 is registered by detector 10. A particularly short response time for the sensor arrangement is obtained by using an accordingly thin sensor layer 2, the thickness of which is preferably less than 100 nm.

For increasing the intensity of light received by detector 10, light waveguide 4 can be provided on its upper flat side with a mirror surface, not shown by the figure, in the area of the end face of light source 6. Thus, a portion of the energy radiated upward is reflected several times and a correspondingly greater coupling of the light emitted by source 6 is achieved. This mirror surface can consist of aluminum which is applied to the end of the light waveguide 4 with a layer thickness of about 0.1 to 0.5 nm. Similarly, the other end of the light waveguide 4 can be provided with such a mirror surface in the vicinity of the end face of the detector 10. To improve the light conduction of waveguide 4 the flat side of the waveguide, facing the carrier, can be provided, in the vicinity of carrier 8, with a reflective layer of metal, preferably aluminum, about 0.1 to 0.5 nm thick. The use of a housing, not shown in the figures, allows the influence of daylight to be eliminated completely.

In order to correct for intensity fluctuation of the light source, an additional detector can be attached to the free flat side of light source 6, and a measurement can thereby be performed using a two-ray method.

Under some conditions, oblique incidence of the light into the light waveguide 4 may be advantageous. This can be accomplished in a simple manner by properly grinding the end face of light source 6 at a desired angle, and, in some circumstances, a corresponding grinding of the end face of the detector 10. This is possible in a simple manner since the light source and the detector are generally cast in a self-harding plastic.

Figure 2:
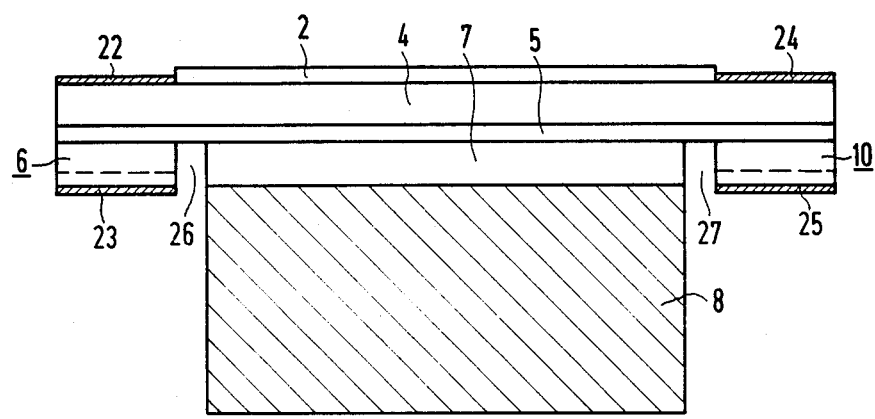
FIG. 2 shows a cross section of an integrated version of the sensor.

In the integrated embodiment of a gas sensor shown in FIG. 2, the sensor layer 2 is arranged with a thickness of about 50 to 200 nm upon a waveguide layer 4 about 5 to 200 nm thick. Waveguide 4 is provided with a matching layer (graded layer) 5 on its lower flat side. Between carrier 8 and graded layer 5, an intermediate semiconductor layer 7 is arranged, which layer can be comprised of a III-V semiconductor compound, particularly gallium arsenide phosphide $(GaAs_{1-x}P_x)$. Light source 6 consists of a light-emitting diode with a semiconductor body of III-V semiconductor compound, particularly gallium asenide phosphide into whose n-conduction semi-conductor body a p-conduction doping substance, preferably zinc (Zn) or magnesium (Mg), is diffused on the lower flat side to a depth of about 3 um. The pn junction produced, not specifically designated in the figure, is indicated as a dashed line. The detector 10 likewise consists of a III-V semiconductor compound, particularly gallium arsenide phosphide $(GaAs_{1-x}P_x)$ in whose n-conduction semiconductor body a pn junction of p-conduction doping substance, especially zinc (Zn), has been produced on the lower flat side, indicated in the figure by a dashed line. Light source 6 is provided with metallic electrodes 22 and 23 which can consists of aluminum vapor-deposited or sputtered onto the corresponding semiconductor layers. Similarly, the detector 10 is provided with electrodes 24 and 25 which can likewise consist of vapor-deposited or sputtered-on aluminum. The metallic electrodes 22, 23, 24 and 25 act as metallic mirrors and thereby improve the coupling of the light into and out of the waveguide.

To increase the intensity of light transmitted, the side of the intermediate semi-conductor layer facing the carrier 8 can preferably be provided with a mirror surface, not shown in the figure. This mirror surface can consist of aluminum which is applied to the intermediate semi-conductor layer with a layer thickness of about 0.1 to 0.5 nm. The graded layer 5 with a thickness of about 10 to 50 nm and the light source 6 as well as the detector 10 can be produced in a simple manner by providing a substrate which will serve as a light waveguide sequentially on one of its flat sides with a graded layer 5 and an intermediate semiconductor layer 7 which initially covers the entire lower flat side of graded layer 5. Subsequently, the entire area is advantageously doped so that the two pn junctions can be produced in a common operation. By moats 26 and 27, the intermediate semiconductor layer 7 is then separated from the light source 6 and the detector 10, respectively. The thin sensor layer 2 can also be centrifuged or sputtered onto the light waveguide 4. For instance, the entire upper flat side of the light waveguide 4 can be provided with the sensor layer first and in the vicinity of the electrodes 22 and 24, this material is removed again by photolithography. After the light source 6 and the detector 10 are provided with their electrodes 22 and 23, 24 and 25, the gas sensor fabricated in this manner is fastened to the carrier 8 with its intermediate semiconductor layer 7 by, for example, cementing.

In the foregoing specification, the invention has been described with reference to an exemplary embodiment thereof. It will, however, be evident that various modifications and changes may be made thereunto to without departing from the broader spirit and scope of the inventions as set forth in the appended claims. The specification and drawings are, accordingly to be regarded in an illustrative rather than in a restrictive sense.

What is claimed is:

1. A sensor for detecting gases and ions comprising: carrier means with at least one flat surface;
light source means with a light emitting surface for generating light and attached to the carrier means so that the light emitting surface of the source is in the same plane as the flat surface of the carrier;
light detector means with a flat detecting surface for detecting and quantifying light falling thereon, attached to the carrier means on the side of the carrier means opposite that to which the source means is attached, the detector being mounted so that its flat detecting surface is in the same plane as the flat surface of the carrier;
light wave guide means with at least one flat side mounted on the flat surface of the carrier, covering the light means, the detector means, and the flat surface with the waveguide's flat side, conveying light of various intensities from said source means to said detector means; and
thin sensor layer means attached to the waveguide means on the side of the waveguide opposite to the side attached to the carrier for analyzing the gases and ions by changing its absorptivity, and thereby altering light flow through the light waveguide means.

2. The sensor of claim 1 further comprising a matching layer placed between the light source means and the light waveguide means for improving the light coupling between the waveguide and the source.

3. The sensor of claim 2 wherein the matching layer is comprised of an ultraviolet-hardening adhesive.

4. The sensor of claim 1 further comprising a matching layer placed between the light waveguide means and the detector means for improving the light coupling between the waveguide means and the detector.

5. The sensor of claim 4 wherein the matching layer is comprised of an ultraviolet-hardening adhesive.

6. The sensor of claim 1 wherein the waveguide means is comprised of a III-V semiconductor compound.

7. The sensor of claim 6 wherein the waveguide is further comprised of gallium phosphide.

8. The sensor of claim 1 wherein the waveguide means is provided with a mirror surface on the side of the waveguide which is attached to the flat surface of the carrier, in the region where the waveguide contacts the carrier.

9. The sensor of claim 8 wherein the waveguide means is provided with a mirror surface on the side of the waveguide which is not attached to the flat surface of the carrier in the region where the light source contacts the waveguide and where the detector contacts the waveguide.

10. The sensor of claim 1, further comprising a second light detector means for monitoring the variability of the light source attached to the light waveguide means on the opposite side of the light waveguide and in the same region where the light source contacts the waveguide.

11. The sensor of claim 1 wherein the light source applies light to the waveguide at a oblique angle.

12. The sensor of claim 1 wherein the thin sensor layer is between 50 and 200 nanometers in thickness.

13. The sensor of claim 1 wherein the thin sensor layer comprises an optical filter with a reversible color change having at least one alkaline or acid color pigment.

14. The sensor of claim 13 wherein the color pigment contains the triphenylmethane system.

15. The sensor of claim 13 wherein the pigment contains malachite-green or crystal-violet lacton.

16. The sensor of claim 13 wherein the sensor layer contains phthaleins or sulfonephthaleins as the pigment.

17. The sensor of claim 13 where the acid color pigment contains bisphenol-A and salicic acid.

18. The sensor of claim 13 wherein the sensor layer contains p-toluidin or p-chloroanilin.

19. The sensor of claim 1 wherein the thin sensor layer comprises an optical filter with a reversible color change having at least one alkaline or acid color pigment and at least one complementary acid or alkaline compound.

20. The sensor of claim 19 wherein the pigment and compound are embedded in a matrix substance.

21. The sensor of claim 1 wherein the sensor layer is comprised at least partially of a chemosensitive material.

22. The sensor of claim 1 wherein the waveguide is between 100 and 400 micrometers thick.

23. The sensor of claim 1 wherein the light source means is a light-emitting diode, the diode and the waveguide both comprising a III-V semiconductor and being fabricated as one unit.

24. The sensor of claim 1 wherein the detector and the waveguide are fabricated as one unit.

25. The sensor of claim 1 wherein the detector contains a pn junction.

26. The sensor of claim 1 wherein the detector contains a metal-semiconductor schottky-type junction.

27. The sensor of claim 1 wherein the light waveguide is of the multimode type.

28. The sensor of claim 1 wherein two moats are etched into the III-V semiconductor material between the light source and the detector for optical insulation.

* * * * *